US 6,562,350 B1

(12) United States Patent
Wang et al.

(10) Patent No.: US 6,562,350 B1
(45) Date of Patent: May 13, 2003

(54) COMBINED VACCINE AGAINST BOTH HAV AND MEASLES VIRUS AND METHOD OF PRODUCING IT

(75) Inventors: Pengfu Wang, Changchun (CN); Jingye Lu, Changchun (CN); Guangpu Li, Changchun (CN); Baosheng Xie, Changchun (CN); Zongming Song, Changchun (CN); Shuyan Li, Changchun (CN)

(73) Assignee: Changchun Institute of Biological Products, Ministry of Public Health (CN)

( * ) Notice: Subject to any disclaimer, the term of this patent is extended or adjusted under 35 U.S.C. 154(b) by 0 days.

(21) Appl. No.: 09/831,752

(22) PCT Filed: Oct. 13, 1999

(86) PCT No.: PCT/CN99/00162

§ 371 (c)(1),
(2), (4) Date: Jul. 6, 2001

(87) PCT Pub. No.: WO00/29018

PCT Pub. Date: May 25, 2000

(30) Foreign Application Priority Data

Nov. 12, 1998 (CN) ........................................ 98124548 A

(51) Int. Cl.[7] .................... A61K 39/295; A61K 39/165; A61K 39/29

(52) U.S. Cl. ................... 424/202.1; 424/204.1; 424/212.1; 424/226.1; 435/173.3; 435/235.1; 435/325

(58) Field of Search ........................... 424/193.1, 202.1, 424/212.1, 226.1, 204.1; 435/173.3, 235.1, 325

(56) References Cited

FOREIGN PATENT DOCUMENTS

| BE | 737945 | 2/1970 |
| CN | 1076726 A | 9/1993 |

OTHER PUBLICATIONS

Fletcher et al., Developments in Biological Standardization (1998) 93 (97–107).*

* cited by examiner

*Primary Examiner*—Laurie Scheiner
(74) *Attorney, Agent, or Firm*—Saliwanchik, Lloyd & Saliwanchik

(57) ABSTRACT

A combined hepatitis A-measles live vaccine, its lyophilized formulations with enhanced storage stability and methods of preparing the same by mixing the viral stocks of hepatitis A virus and measles virus or by propagating the two viruses on same diploid cell substrate are disclosed. The combined live vaccine thus prepared is a useful vaccine for preventing the infections with hepatitis A and measles without causing any interference between antigenicity of the two viruses and any serious adverse events due to their mixing or co-culturing.

16 Claims, No Drawings

COMBINED VACCINE AGAINST BOTH HAV AND MEASLES VIRUS AND METHOD OF PRODUCING IT

FIELD OF THE INVENTION

The present invention relates to a combined vaccine, its production and use, in particularly to hepatitis A-measles combined vaccine formulations comprising prophylactically effective titers of hepatitis A virus (HAV) and measles virus (MV) as virus components, and stabilizer components which is effective for stabilizing the virus components. The combined vaccine does not induce any interference on the immune response and the immunogenicity of the two viruses and having excellent storage stability, so that the combined vaccine could be stored at ambient temperature for a long time and could be used for preventing recipients, especially intants and young children against the two infections diseases. The present invention further relates to methods of making the combined vaccines which are lyophilized or unlyophilized by mixing the two different viruses or by propagating the two different viruses on a same diploid cell substrate.

BACKGROUND OF THE INVENTION

As well known that, immunization to protect against communicable disease is one of the most successful and cost-effective practices of modern medicine. In order to total control over the entire vaccination chain leading to increased social acceptance and use of vaccine in all countries and regions, especially in developing countries and regions, the measures including providing newer, polyvalent, more stable and cost-effective vaccines must be taken. For this purpose, so much research efforts for developing newer vaccines and vaccines having improved stability has been extensively made in many laboratories of the world, since the "Children's Vaccine Initiative" (CVI) had founded by United Nations Children's Fund (UNCF) and World Health Organization (WHO) in 1991. Therein, much attention is focused on making vaccine more user-friendly through development of combined vaccine and the introduction of less invasive inoculation technigues.

Popularization of the combined vaccines reduced the nember and manufacturing cost of vaccines, and increased immunity levels against disease, so that it has greatly increased vaccine coverage in the world, especially in developing countries including China.

Many combined vaccine have been licensed and used in immunization practices, for example in the past several decades a routine vaccination schedule for infants and children has included immunization with a live attenuated trivalent vaccine (MMR) for measles, mupms and rubella, and live trivalent vaccine (DTP) for diphtheria, tetanus and pertussis and so on. Recently, a haemophilus b conjugate vaccine combined by reconstitution with diphtheria and tetanus toxoids and acellular pertussis vaccine (DTaP-Hib) for use as fourth dose in childhood vaccination series has licenced by Food and Drug Administration (FDA) in the United States. Also, TriHlBit (Trademark) will be the first vaccine to be licensed combined vaccine in U.S. that combines PTaP with a haemophilus b conjugate vaccine. However, there has been no reports on combined vaccine comprising hepatitis A and measles viruses and on processes of making combined vaccine by propagating two or more different viruses on a same cells substrates.

SUMMARY OF THE INVENTION

The present invention provides a combined hepatitis A-measles vaccine (HM) comprising prophylactically effective titers of attenuated hepatitis A live virus and prophylactically effective titers of attenuated measles live virus, and with or without stabilizer for the viruses, by means of which vaccine the infection associated with hepatitis A virus and measles virus can be prevented without causing any interference between antigenicity of the two viruses due to their mixing or co-culturing.

The combined hepatitis A-measles vaccine according to the present invention, wherein the viral titers of hepatitis A virus is not less than $10^{6.0}$ $CCID_{50}$/ml (50% cell culture infectious dose per milliliter of virus stock), and the viral titers of measles virus is not less than $10^{3.5}$ $CCLD_{50}$/ml.

Within the scope of the present invention, the combined hapatitis A-measles vaccine is provided in the form of lyophilized or unlyophilized.

The present invention further provides a stabilized combined hepatitis A-measles vaccine formulation comprising virus components and stabilizer components, wherein the virus components comprise prophylactically effective titers of hepatitis A live virus and measles live virus, and the stabilizer components consisting essentially of from 0 to 2% (w/v) of human serum albumin (HSA), from 0.5 to 1.1% (w/v) of gelatin, from 5 to 10%(w/v) of trehalose, from 0.75 to 1.5% (w/v) of sodium glutamate, from 0.05 to 0.5% (w/v) of ascorbic acid, from 0.5 to 2.8% (w/v) of urea, from 5 to 10% (w/v) of mannitol or sorbitol or a 1:1 mixture of them, and from 0.5 to 1% (w/v) of nositol in terms of the concentrations in the stabilized live vaccine formulation prior to lyophilization, and wherein the stabilized combined vaccine optionally lyophilized or unlyophilized.

According to the present invention, there is provided a method of preparing combined hepatitis A-measles vaccine comprising mixing a stock material of attenuated hepatitis A live virus having viral titers of not less than $10^{7.0}$ $CCID_{50}$/ml with a stock material of attenuated measles live vaccine having viral titers of not less than $10^{4.5}$ $CCID_{50}$/ml at a suitable ratio, to thereby obtain a combined vaccine stock suspension, in which the viral titers of said hepatitis A virus is not less than $10^{6.5}$ $CCID_{50}$/ml and the viral titers of said measles virus is not less than $10^{4.0}$ $CCID_{50}$/ml.

The combined vaccine thus prepared is a useful vaccine which can be used to prevent the infections with both hepatitis A and measles without any reduction in immunogenic potencies and any deterioration of its properties. Moreover, the combined vaccine never caused interference between viral antigenecities due to their mixing, which interference is frequently abserved, in particulr in case of combined vaccine for animals.

According to the present invention, the present inventors are able to provide another method of preparing the combined hepatitis A-measles vaccine, comprising following steps:

(a) providing seed viruses of hepatitis A virus and measles virus previously prepared, respectively;

(b) inoculating the seed virus of hepatitis A virus obtained from step (a) into a human fetal lung diploid fibroblast cell cultures and following by culturing the cells to propagate the virus;

(c) when the positive hepatitis A virus-infected cells are more than 75%, inoculating the seed virus of measles virus obtained from step (a) into the same cell monolayers on which the hepatitis A virus have propagated, and the cells are cultured continuously;

(d) At the time when the positive hepatitis A virus-infected cells are more than 90% as detected in terms of immunofluoresence (IF) and the positive measles virus-infected cells are more than 90% as detected in terms of cytopathogenic effect (CPE), the cells infected with the two viruses are harvested and the vaccine stock materials containing the two viruses are collected to thereby obtain the desired combined vaccife.

In a preferred embodiment of the present invention, wherein the positive infectious rates on the diploid cells and viral titers of hepatitis A virus are detected by HAV-specific detection systems comprising immunofluorescence and enzyme-linked immunosorbent assay.

In a more preferred embodiment of the present invention, the method defined as above furthermore comprising suitable mixing the stock material of combined hepatitis A-measles vaccine obtained above with a stabilizer for attenuated live vaccine at about 1:1 volume ratio and then lyophilizing the resultant formulation thereby to obtain a lyophilized preparation of the combined hepatitis A-measles vaccine.

According to a preferred embodiment of the present invention, said stabilizer consisting essentially of from 0 to 2% (w/v) of human serum albumin, from 0.5 to 1% (w/v) of gelatin, from 5 to 10% (w/v) of trehalose, from 0.75 to 1.5% (w/v) of sodium glutamate, from 0.05 to 0.55% (w/v) of ascorbic acid, from 0.5 to 2.8% (w/v) of urea, from 5 to 10% (w/v) of mannitol or sorbitol or a 1:1 mixture of them, and from 0.5 to 1% (w/v) of inositol, in terms of the concentrations in the lyophilized live vaccine formulation.

The present invention still further provides a method of preparing lyophilized combined hepatitis A-measles vaccine, comprising following steps:

(a) providing stock materials comprising prophylactically effective titers of attenuated hepatitis A live virus and of attenuated measles live virus respectively, and then mixing them to obtain a mixed vaccine stock;

(b) adding a stabilizer stock solution to the mixed vaccine stock of step (a) at about 1:1 (v/v) ratio and mixing them together to obtain a combined vaccine formulation;

(c) lyophilizing the combined vaccine formulation obtained from the step (b).

According to a preferred embodiment of the present invention, the lyophilization step (c) involves precooling the combined vaccine formulation in the form of aqueous suspension to below the eutectic point temperature of the suspension over 3 to 6 hrs, and then gradually increasing the temperature from −35 to 35° C. over 8 to 20 hrs to removing water from the cooled suspension by sublimation.

In a particularly preferred embodiment of the present invention, the prophylactically effective titers of attenuated hepatitis A virus is not less than $10^{6.0}$ $CCID_{50}$/ml, and the prophylactically effective, titers of attenuated measles virus is not less than $10^{3.5}$ $CCID_{50}$/ml in the lyophilized combined vaccine.

DETAIL DESCRIPTION OF THE INVENTION

Essentially, according to the present invention, there is provided a combined hepatitis A-measles vaccine consisting of prophylactically effective titers of attenuated live HAV and attenuated live MV, which does not induce any incompatibilities or mutual interference on immune response and immunogenicity between the two viral antigens, and which optionally contains a stabilizer or lyoprotectant.

Measles is the most contagious disease know to man host caused by measles virus (MV). Immunity to measles following an attack of the desease appears to be lifelong.

Following measles vaccine, immunity is similarly of many years duration and probably lifelong. The majority of measles cases occur in persons who have not been immunized against measles, and there are small number of people who do not respond to a single dose of measles vaccine. For this reason, since 1989, the recommendation for two does of measles vaccine was made. Therefore, all young children age one year and older should receive a dose of measles vaccine, and the second dose of measles vaccine should be given upon school entry (age 4–6 years) or at 10 to 11 years of age. In addition, persons entering collage, the military, and health profession schools or those who lack a history of childhood illness or immunization should receive a second dose of vaccine. In view of the age shift upward of measles infections, it is particularly important that adolescents returning to school this fall be up-to-date with two doses of measles vaccine.

Hepatitis A (HA) is a worldwide distributive acute communicable discase caused by intection with hepatitis A virus (HAV). Like other enteric deseases mainly transmitted through a faecal/oral route, hepatitis A is typically a childhood infection associated with poor and overcrowded conditions. Athough children hepatitis A is generally very mild, young children play an important role in the transmission of hepatitis A virus because a child with a subclinical infection can pass the virus to non-immune individuals. While improved sanitation and living condition have led to a reduced circution of the virus among some groups of population, younger generations are still susceptible to infection and can act as foci of hepatitis A outbreaks. Vaccination of children attending day-care centers, who live in areas with elevated anti-HAV seroprovalence, has been shown to be of benefit, and it has been suggested that routine hepatitis A vaccination program of children would be the most effective means of controlling HAV infection.

In view of considerable similarity of HAV and MV in epidemiological aspects and a similar two-dose immunization schedule of both hepatitis A and measles vaccine, the desirability and availability of combined hepatitis A-measles vaccine are in evidence.

Up to now, the live measles vaccine generally used in China has been developed from the isolated Chang-47 and Hu-191 strains which have adapted to passage in vitro in primary culture of chick embryo cells. However, studies of the present inventors found that human fetal lung diploid cell monolayers or cell suspension used as cell substrates will advantageous to propagation of the virus and maintenance of viral antigenicity, and also prevented the contamination from exogenous factors, for example egg protein and the like.

On the other hand, the hepatitis A live vaccine has been developed from wide-type HAV strain L-A-1 isolated from stool of a patient by serial passaging in vitro in human diploid fibroblast cells by the precent inventors, and which have been licensed for practical use and industrial-scale production in China. More than 80 milions individuals who are at high risk of hepatitis A exposure received inoculation of the vaccine so far, and the follow-up study results showed a 85% seroprotection rate after primary dose, and a 100% seroprotection rate after the only booster injection.

During their long-term studies and production practies, the present inventors had found that the human fetal lung diploid fibroblast cells (strain 2BS) are exellent host not only for hepatitis A virus, but also for measles virus, and that the measles virus exhibited a more rapidly propagation rates on these cell substrates. In particularly, the present inventors had unexpectedly found that, after inoculating a seed virus of HAV into the diploid cell culture and culturing the cells in a culture medium for 2–3 weeks, an additional inoculation and cultivation of measles virus can be performed, while the infectious potency of HAV achieved a sufficiently high level. After about one additional week, the two viruses could be almost simultaneously harvested in a high recovery and in high intectious potencies. This finding constituted the basis of preparing combined HM vaccine of the invention by propagating the two attenuated live viruses on the same host cell substrate.

In the case of preparing the stock materials of HAV and MV, the respective stock materials of live virus can be diluted and mixed at a suitabe volume ratio, to thereby obtain a combined live vaccine. in the form of aqueous suspension comprising prophylactically effective titers of HAV and MV. Herein, the prophylactically effective titers are refer to a viral potency of not less than $10^6$ CCID$_{50}$ for HAV and of not less than $10^{3.5}$ CCID$_{50}$ for MV.

The present invention further provides a method of preparing combined hepatitis A-measles vaccine, comprising following steps:
  (a) providing seed viruses of attenuated hepatitis A live virus and attenuated measles live virus, respectively;
  (b) inoculating the seed virus of hepatitis A virus obtained from the step (a) into a human fetal lung diploid fibroblast cell cultures and following by culturing the cells to propagate the virus;
  (c) When the positive hepatitis A virus-infected cells are more than 75%, inoculating the seed virus of measles virus obtained from the step (a) into the same cell monolayers on which the hepatitis A virus had propagated, and the cells are cultured continuasly;
  (d) At the time when the positive hepatitis A virus-infected cell are more than 90% as detected in terms of immunofluorescence and the positive measles virus-infected cells are more than 90% as detected in terms of cytopatliogenic effect, the cells infected with the two viruses are harvested and the vaccine stock materials containing the two viruses are collected to thereby obtain the desired combined vaccine.

For preparation of the combined HM vaccine, according to the present invention, the vaccine stock material of HAV can be prepared from HAV strain L-A-1 by the method described in CN Patent No.92114998.0, and the vaccine stock material of MV can be prepared from MV strain Chang-47 by a conventional process in accordance with the "Reguirement for Measles Vaccine, live" in Chinese Reguirements for Bioloical Products.

HAV isolated from clinical materials can grow and propagate in many types of cultured cell culture, though the relative propagation coefficient is lower, and can not lead to a morphologically visual cytopathic changes. By contract, MV can grow and propagate in many types of primary cell culture or subculture in a relatively shoter replication cycle and the typical multinucleate giant cells as well as other similar cyto-morphological changes can be bserved on microscopic examination. The present inventors have showed that human diploid cells are exellent susceptible host for both HAV and MV, so the diploid cell line 2BS is chose as a preferred common host cell used for preparation of the combined HM vaccine of the present invention.

To prepare the combined hepatitis A-measles vaccine, a human diploid cell line 2BS is cultured for growth and maintenance of the cells, and to form a dense confluent cell monolayer in a roller bottle apparatus. Then, a seed virus of HAV is inoculated into the cell culture at a multiplicity of infection (m.o.i.) of 0.02–10 and followed by culturing at about 32–35° C. During the culturing of the virus, the area of the infected cells gradually expands in accordance with the propagation of virus and the percentage area of the positive intected cells are monitored by immunofluorescence.

After about 2–3 weeks when more than 75% of HAV-intected cells occurred positive immunofluorescence, change the midium to a nutrient midium containing 10% fetal calf serum (FCS) or 0.01–0.25% (w/v) HSA, and a seed virus of MV strain is additionally inoculated into the same cell culture at a m.o.i. of 0.01 to 10. Then, the human diploid cell culture infected with both HAV and MV is cultured continuasly with renewed the midium at 3–5 days intervals, and examined morphological changes of the cells day by day. The specific morphological changes of the MV-infected cells as the so-called cytopathogenic effect (CPE) and thus the degree of virus growth can be determind. At the time when the CPE is observed almost throughout the entire region of the cell culture monolayer (about 90%) and the positive HAV-infected cells are also more than about 90%, the virus culturing is terminated. Thereafter, the cell culture is placed at 2–8° C. for 1–3 days for cold release of the viruses, and then the infected cells can be collected and stored frozen at the temperature of below −20° C.

After thawing the cells, the resultant cell suspension is subjected to three cycles of freeze-thawing and subsequently to sonification in a ice water bath for disruption of the cells, followed by centrifugation to remove the cell debris and to separate a supernatant from the suspension. The supernatant containing HAV and MV is collected to obtain a stock material of the combined hepatitis A-measles vaccine.

It is evident that, as mentioned above, the combined HM vaccine can be obtained by a simply mixing process. For the preparation of the mixed vaccine, respective stock material of live vaccines are diluted and mixed so that the dosage levels of each virus maintain a generally fixed antigenic activity employed to elicit an immune response against infection of the viruses.

The present invention still further provides a method of preparing lyophilized combined hepatitis A-measles vaccine, comprising following steps:
  (a) providing stock materials containing prophylactically effective titers of attenuated hepatitis A live virus and of attenuated measles live virus respectively, and mixing them to obtain a mixed vaccine stock;
  (b) adding stock solution of a stabilizer to the mixed vaccine stock of step (a) at about 1:1 volume ratio and mixing them together to obtain a combined vaccine formulation;
  (c) lyophilizing the combined vaccine formulation obtained from the step (b).

In a preferred embodiment, the stock materials of HAV and MV and stabilizer for the lyophilized combined vaccine can be suitable diluted and mixed at about 1:1 (v/v) ratio, and then the resultant aqueous formulation comprising prophylactically effective titers of HAV and MV and stabilizer included in the vaccine formulation at a concentration sufficient to stabilize the viruses againt heat inactivation can be lyophilized, so that the combined HM vaccine thus obtained can be preserved at ambient temperature for a long-term without loss of their infectious potencies, thereby to offer more convenience, potentially better compliance and lower administration costs.

The stabilizer of an attenuated live vaccine can be formulated by a simple mixing each of the components except HSA, and preheating the resultant mixture at about 37° C. for 24–48 hrs, then cooling the mixture solution to about 32° C. and adding HSA which has been sterilized by a series of ultrafiltration into the mixture solution.

Thereafter, the stabilizer thus obtained can be mixed with virus stock of the combined HM vaccine at a suitable ratio, for example at about 1:1 (v/v) ratio.

However, one of ordinary skill in the art will be well aware that changing volume ratio of stabilizer to vaccine may be applied to practice the claimed invention, which in turn will require changes to the concentration of stabilizer components. The invention not ony limited to the specified 1:1 stabilizer/virus combination to generate the final vaccine formulation for lyophilization. Therefore, the artisan may shose different ratio or use the stock of viral preparation with altered concentration of chemical components which used in preparing stabilizer.

After the vaccine is formulated, the resultant aqueous suspension of the combined vaccine can be dried by lyophilization. Briefly, lyohilization involves the step of pre-cooling the aqueous suspension at below the eutectic point temperature (below −30° C.) of the aqueous suspension for about 3–6 hrs, and then removing water from the cooled suspension by sublimation to form a lyophilized vaccine. Within one preferred embodiment, aliquots of the formulated vaccine suspension are subjected a multistep freeze-drying procedure in a refrigerated chamber of the freeze-drying apparatus during a period of 8–20 hrs with gradually uprise of the temperature from about −35° C. to 35° C.

In order to demonstrate improvement in thermo-stability and storage stability of live vaccine resulted from the presence of stabilizer, the present invention is exemplified by the combined HM vaccine, for example by detecting viral titers pre- and post-lyophilization of the combined HM vaccine, to observe the effectiveness of stabilizer on storage stability of the combined live vaccine. The results show that the stabilizer included in the vaccine formulation of the present invention at a concentration sufficient to stabilize the live virus vaccine against heat inactivation remarkably improved thermal stability of the. vaccine which has been lyophilized as measured by the $CCID_{50}$, as compared with control vaccine formuation without stabilizer therein.

In a especially preferred embodiment, the stabilizer is essentially composed of from 0 to 2% (w/v) of human serum albumin, from 0.5 to 1% (w/v) of geltion, from 5 to 10% (w/v) of trehalose, from 0.75 to 1.5% (w/v) of sodium glutamate, from 0.05 to 0.55% (w/v) of ascorbic acid, from 0.5 to 2.8% (w/v) of urea, from 5 to 10% (w/v) of mannitol or sorbitol or a 1:1 tixture of them, and from 0.5 to 1% (w/v) of inositol, in terms of the concentrations in the lyophilized live vaccine formulation.

In a comparason experiment, the present inventors found that a similar result can be observed when a stabilizer solution which minus HSA compnent is used in a live virus (especially some envelope-free viruses, for exmaple HAV, MV, and poliovirus) vaccine formulation if the lyophilization cycle parameters could be suitable adjusted.

It can be show experimentally that the combined hepatitis A-measles vaccine of the present invention exhibited a exellent specificity as demonstrated in vitro by serum neutralization (NT) test or virus identification test of MA and HAV. The results indicated that the HAV and MV viruses included in the combined vaccine formulation of the present invention at an adentifiable infectious dose can be completely neutralized by respective specific antisera.

Further, the combined HM vaccine is used to inoculate rhesus monkeys and a series of experiments in viro have done for evidence of its safty and imunogenicity in these higher primates. It have been found that the aminals receved the vaccine are entirely free from paralysis or any other localizing symptoms of central nervous system (CNS), and none of the animals have evidence of histopathologic changes in CNS and hepatic tissue. Egually important, there are no histologic changes that are temporarily related to seroconversion in the infected animals, and also no abnormal elevation of live enzymes which attributable to the inoculum. On the other hand, it has been proved that all of five animals infected with both HAV and MV are developed IgM anti-HAV and IgM anti-MV detectable by enzyme linked immunosarbent assay (ELISA) on weeks 2 to 4 following inoculation, and the serum antibodies are disappeared at weeks eight and nine.

Furthermore, half of animals are developed both specific anti-HAV antibody and anti-MV hemagglutination inhibition (IH) antibody on week two, and the seroconversion rates (sero-prevalences) of both anti-HAV and anti-MV are 100% on week four post-inoculation. Finally, in order to futher demostrate effectiveness and clinical utility of the combined hepatitis A-measles divalent live vaccine, a clinical trial is conducted in which the live hepatitis A vaccine is administered concomitantly with the live measles vaccine, and compared to single administration of monovalent hepatitis A vaccine and monovalent measles vaccine which have been licensed for general distribution in China.

A total of 275 healthy intants aged 8 to 12 months are divided into three groups, and are given one dose of hepatitis A vaccine with measles vaccine, single hepatitis A vaccine and single measles vaccine respectively, for comparing clinical and antibody responses to these three vaccination schemes. During 72 hrs of observation period post-inoculation, none of these subjects occurred both local and general reactions, and there are no significant difference in the rate of adverse events between the groups simultaneous or single administration of HA vaccine and measles vaccine. Especially, between the two groups of receiving either HA vaccine or measles vaccine and combined NM vaccine, no statistically significant differences are observed in the positive seroconversion rates for anti-HAV and anti-MV, and in the geometric mean titers (GMTs) of anti-HAV and anti-MV antibodies, as measured by a modifred ELISA assay.

In summry, both hepatitis A live vaccine and measles live vaccine not only have a similar vaccination schedules for intants and young children, but also without any mutual interference in the immune response and the immunogenicity as demonstrated using identical immunoassay for evoluation. The results as described in Example 4 and 5 of the specification confirmed the outstanding safety and immunogenicity of the combined HM vaccine and support its use in preexposure prophylaxis against the two viruses intection. Therefore, it is expected that the combined hepatitis A-measles vaccine can be prepared from virus stocks of HAV and MV by the methods outlined as above which involves much more techniques than the simple mixing of existing viral antigens, for example co-cultivation of two or more attenuated live viruses on a same cell culture, even though there are many probable problems came from viral genetics and molecular biology remain to be resolved, and would be incorporated into the Children's Vaccine Initiative for simplifying the implementation, increasing the acceptance and improving the control of the two deseases.

In accordance with the present invention, the combined hepatitis A-measles live vaccine as first dose could be administered to infants aged between 10 to 13 months to provide dual protection against hepatitis A and measles, or as boost dose to young children upon school entry (age 4 to years) or at 10 to 11 years of age. In addition, persons entering college, the military and health profession schools or those lock a history of childhood illness or immunization should receive a second dose of the combined vaccine. In view of age shift upward of measles and hepatitis A infections, it is particularly important that adolescents returning to school with two doses of the combined vaccine.

PREFERRED EMBODIMENT OF THE INVENTION

The present invention will be further illustrated in more detail with reference to the following Examples. It is to be understood, however, that the examples should not be construed as limitation of the scope of the present invention.

EXAMPLE 1

Preparation of Combined Hepatitis A-measles Vaccine

Human fetal lung diploid fibroblast cells (2BS) are cultured at 37° C. using Eagle's Minimum Essential Medium (EMEM) for both growth and maintenance of the cells. After five days, a seed virus of the hepatitis A virus strain L-A-1 decribed in CN Patent No. 92114998.0 is plated on confluent cell monolayers of the diploid cells at a m.o.i. of about 4.5, followed by continuas culturing for 3 weeks using a maintenance midium (EMEM containing 2–5% FCS) which renewed at one week intervals, and the positive HAV-infected cells are periodically monitored by the indirect immunofluorescence assay (IFA). After three weeks, at the time when about 75% of HAV-intected cells occurred a positive immunofluorescence, changing the medium to a fresh nutrient midium supplemented with 10% FCS, and a seed virus of measles virus strain Chang-47 is additionally inoculated into the same cell culture at a m.o.i. of about 4.5.

Subsequently, the human diploid cell culture infected with both HAV and MV is continuasly cultured at 33–35° C. with renewed the midium every five days and sampled daily for morphological microscopic examination. When the typical cytopathic effect (CPE) is observed (multinucleated giant cell) in about 50% MV-infected cells, the nutrient medium is discarded from culturing vessel and the residual FCS is washed away by a balanced salt solution. Then, the cells are resuspended in Eagle's MEM medium without FCS and cultured continuasly. At the time when the HAV-infected cells are more than 90%, and MV-infected cells achieved about 95%, the virus culturing is terminated and the cells are placed under 2–8° C for 72 hrs to release cell-bound HAV and MV, and then cryopreserved at below –20° C.

The cell stored frozen are subjected to three cycles of freeze-thawing and to sonification (10–15 min) for disruption of the cells, followed by centrifugation (2,000 rpm, 4° C., 15 min) for clarifying of the cell debris, and then the supernatant is collected to obtain virus stock containing live HAV and MV.

EXAMPLE 2

Preparation of Lyophilized Combined Hepatitis A-measles Vaccine

The stabilizer for lyophilized combined HM vaccine can be formulated as following:

0.8 g of purified gelatin is dissolved in 30 ml of boiled distilled water and the resultant solution is sterilized in autoclave at: 116° C. for 40 min. After cooling the solution to room temperature, adding 1.0 g of HSA which have been sterilized by a series of ultrafiltration through a 0.22 μm millpore filter into the solution of gelatin to obtain a gelatin-HSA solution. Meanwhile, 8.0 g of trehalose, 1.0 g of sodium glutamate, 0.1 g of ascorbic acid, 2.5 g of urea, 8.0 g of sorbitol and 0.6 g of inositol are added in this order to 50 ml of distilled, water, and the resultant mixture is preheated at 37° C. for 24 hrs with stirring. On the next day, the mixture is added to the gelation-HSA solution, and then distilled water is added thereto to make the total volume to 100 ml. The pH of the resultant: mixture solution is adjusted to about 7.0 by 0.1N HCl, and subjected to ultrafiltration sterilization, to obtain desired stabilizer stock solution.

The stabilizer stock solution is mixed with stock suspension of the combined HM vaccine prepared in Example 1 at about I1:1 (v/v) ratio to generate the final combined vaccine formulation. Therein, the stabilizer being present at a concentration sufficient to stbilize the viruses against heat inactivation.

Then, the vaccine formulation is aliquoted into 2 ml glass vial (1.2 ml/vial) and placed the vials into a lyophilizer (model FS 150-SS 20C, Hull Co., USA) for multistep lyophilization cycle: precooling at −40° C. for 4 hrs, then the shelf temperature is gradually increased to 32° C. and drying under vacuum for 15 hrs, thereby to obtain a lyophilized combined hepatitis A-measles vaccine.

EXAMPLE 3

Storage Stability Testing of Lyophilized Combined Hepatitis A-measles Live Vaccine The experiment is carried out using five consecutive production lots of combined HM live vaccine, the samples of the vaccine are stored at 2–8° C., 25° C. and 37° C. for different periods and then the viral titers of HAV and MV in the conbined divalent vaccine are determined, respectively.

Because the presence of cytopathic effect (CPE) in diploid cells caused by measles virus, the measles virus must be neutralized before detecting the viral titers of HAV. For this purpose, the samples of combined vaccine to be lyophilized are ten-fold serially diluted, the sample (0.1 ml) at $10^{-2}$ dilution is added into a diluted specific anti-MV serum (0.9 ml) and then the resultant mixture is incubated overnight at 2–8° C. On the next day, the neutralized vaccine samples are ten-fold serially diluted, and the sample at $10^{-3}$ to $10^{-8}$ dilution is plated on confluent diploid cell monolayers, then the cells are cultured. After 4 weeks, the cells are harvested and disrupted by methods described as above. The supernatant collected by centrafugation is used for detecting viral titers of HAV in a ELISA assay. The values (Log $CCID_{50}$/ml) are determined accordingly using the method of Reed and Muench (Reed, L. J. and Muench, H., Am. J. Hyg. 27:493–497, 1938).

On the other hand, in order to determine the viral titers of measles virus present in the lyophilized combined HM vaccine, the respective samples of the combined vaccine and standards of measles virus (provided by National Institute for the Control of Pharmaceutical and Biological Products, Beijing, China) are ten-fold serially diluted, and the sample at $10^{-2}$ to $10^{-6}$ dilution is inoculated on Vero cell culture, and the cells are cultured at 34° C. for one week.

After completion of the cultivation, the viral titers are determined by conventional method described as above. The resuts are showed in following Table 1 and Table 2.

TABLE 1

Comparision of viral titers of HAV and MV
in the combined HM vaccine Pre- and post-lyophilization

|  | Pre-lyophilization | | Post-lyophilization | |
|---|---|---|---|---|
| lots | HAV | MV | HAV | MV |
| 1 | 7.0* | 5.38 | 6.50 | 5.13 |
| 2 | 6.50 | 5.38 | 6.33 | 5.50 |
| 3 | 6.50 | 6.13 | 6.00 | 5.75 |
| 4 | 6.67 | 5.50 | 6.33 | 5.38 |
| 5 | 6.50 | 5.00 | 6.30 | 4.63 |

*The data given in the table represent viral titers expressed in logarithm value of 50% cell culture infectious dose per milliliter of virus stock (log $CCID_{50}$/ml).

TABLE 2

Comparision of viral titers of
HAV and MV in lyophilized combined
HM vaccine after storage at different
temperatures for different periods

| lots | 2–8° C., HAV | 0 day MV | 2–8° C., HAV | 12 months MV | 25° C., HAV | 3 months MV | 37° C., HAV | 7 days MV |
|---|---|---|---|---|---|---|---|---|
| 1 | 6.50* | 5.13 | 6.50 | 5.13 | 6.67 | 5.38 | 6.50 | 5.00 |
| 2 | 6.33 | 5.50 | 6.50 | 5.63 | 6.33 | 5.50 | 6.50 | 5.63 |
| 3 | 6.00 | 5.75 | 6.00 | 5.88 | 6.33 | 5.63 | 6.33 | 5.75 |
| 4 | 6.33 | 5.38 | 6.00 | 5.13 | 6.00 | 5.13 | 6.33 | 5.38 |
| 5 | 6.33 | 4.63 | 6.33 | 4.63 | 6.33 | 4.75 | 6.00 | 4.75 |

*The data given in the table represent viral titers expressed in logarithm value of 50% cell culture infectious dose per milliliter of virus stock (log $CCID_{50}$/ml).

It is can be seen from the data as showed in Table 1 and Table 2, in the presence of stabilizer for lyophilization, though total five lots of combined HM vaccine exhibited a slight decrease in viral titers measured as the log $CCID_{50}$ post-lyophilization storage at the indicated temperatures for indicated periods, the decreases are less than 0.5 log as compared to the vaccine in its initial lyophilization state (stored at 2–8° C. for 0 day). Further, the samples of lyophilized combined HM vaccine of the present invention which have been stored at 2–8° C. for 12 months, at room temperature (25° C.) for 3 months, and at 37° C. for 7 days respectively, both HAV and MV contained in the combined vaccine exhibited a exellent storage stability offered by the stabilizer subsequent to lyophilization.

EXAMPLE 4

Animal Experiments for Demonstrating Safty and Immunogenicity of the Combined Divalent HM Vaccine In this example, rhesus monkeys, the susceptible animal are chosen at random as experimental subjects. Immunized animals are used in viro to evoluate safty and immunogenicity of the combined HM vaccine. The lyophilized combined vaccine formulation prepared in accordance with the method described in Example 1 is intravenously (1.0 ml) and intracranially (0.5 ml) administered to rhesus monkeys (each group comprising 5 animals). In the experiments, both monovalent hepatitis A vaccine and monovalent measles vaccine are used as control vaccines.

After inoculation, local and general reaction including paralysis and other serious adverse events attributed to the damage of CNS caused by infection of MV are observed and recorded every day for 21 days. Histologic sections prepared from serial liver biopsies obtained from the animals by intrahepatic puncture are evoluated for histopathologic changes. The changes of liver enzyme (glutamic-pyruvic transaminase, GPT) levels are used for evaluating the damage of lever caused by infection of HAV.

The biochemical and histological investigations show that none of rhesus monkeys has elevation of live enzyme attributable to the combined HM vaccine inoculum, and none of the animals from experimental groups has evidence of histopathologic changes in brain tissue and liver tissue more than those seen in pre-inoculation biopsies or in parallel monovalent vaccine vaccination group. Equally, there are no biochemical and histological changes that are temporally related to seroconversion in brain and hepatic tissues of HM vaccine inoculated animals.

The sera of the immunized animals are tested by hemagglutination-inhibition (HI), neutralization (TN), and enzyme immunoassay (EIA) methods. For neutralization test, the sera to be tested are diluted in different dilution in culture media and inactivated for 30 min at 56° C. in a water bath. 100 µl of each dilution is mixed with equal volume of HAV or MV suspension containing 100 $CCID_{50}$/ml. The serum-virus mixture are incubated overnight at 4° C. to perform neutralization reaction. Thereafter, 100 µl of neutralized products are inoculated on the diphloid cell monolayers. Each serum is tested in parallels. After 2 hrs at 35° C. to allow adsorption, 15 µof culture media are added. The the plates are incubated at 35° C. for 28 days. At days 7, 14 and 28, the plates are frozen at below –20° C. and thawed for cold releasing of the virus.

Then, 100 µl of each cell culture is transferred to other plates for detection of HAV or MV by a immunoassay. (Groen, et al., J. Virological Methods 23:195–203, 1989). HI and EIA are performed, and the respective seroconversion rates of anti-HAV and anti-MV are determed pairwise.

The results are summarized in Table 3 and 4 as below. The data given in Table 3 showed the serum GPT enzyme levels at weeks 0, 2, 4 post-inoculation of the combined HM vaccine from lots 1, 3 and 5. A serum GPT (SGPT) level of $\geq 25$ U/ml is considered to be abnormal elevation of the liver enzyme, and the seroconversion rates of the two antibodies are expressed as seroconversion rates for 5 animals at weeks 0, 2, 4 after-inoculation.

TABLE 3

SGPT abnormal elevation and seroconversion
raters of anti-HAV and anti-MV at weeks 0,
2, 4 post-inoculation in initially seronegative animals

| | | | | seroconversion rates | | | | | |
|---|---|---|---|---|---|---|---|---|---|
| Sample | SGPT elevation | | | anti-HAV | | | anti-MV (H1 Ab) | | |
| lots | 0* | 2 | 4 | 0 | 2 | 4 | 0 | 2 | 4 |
| HM-1 | 0/5** | 0/5 | 0/5 | 0/5** | 3/5 | 5/5 | 0/5** | 4/5 | 5/5 |
| HM-3 | 0/5 | 0/5 | 0/5 | 0/5 | 3/5 | 5/5 | 0/5 | 4/5 | 5/5 |

TABLE 3-continued

SGPT abnormal elevation and seroconversion
raters of anti-HAV and anti-MV at weeks 0,
2, 4 post-inoculation in initially seronegative animals

| Sample | SGPT elevation | | | seroconversion rates | | | | | |
|---|---|---|---|---|---|---|---|---|---|
| | | | | anti-HAV | | | anti-MV (H1 Ab) | | |
| lots | 0* | 2 | 4 | 0 | 2 | 4 | 0 | 2 | 4 |
| HM-5 | 0/5 | 0/5 | 0/5 | 0/5 | 3/5 | 4/5 | 0/5 | 4/5 | 5/5 |
| HAV | 0/5 | 0/5 | 0/5 | 0/5 | 3/5 | 5/5 | | | |
| MV | 0/5 | 0/5 | 0/5 | | | | 0/5 | 4/5 | 5/5 |

*Weeks of post-inoculation.
**the data represent positive rates for each group of 5 animals.

TABLE 4

Titers of serum neutralizing antibody
in amimals pre- and post-inoculation

| | Anti-HAV | | | | Anti-MV | | | |
|---|---|---|---|---|---|---|---|---|
| Sample | Pre-inocu- | Post-inoculation | | | Pre-inocu- | Post-inoculation | | |
| lots | lation | 1:2* | 1:4 | 1:8 | lation | 1:2* | 1:4 | 1:8 |
| HM-1 | + | − | − | + | + | − | − | + |
| HM-2 | + | − | − | + | + | − | − | + |
| HM-3 | + | − | − | + | + | − | − | + |
| HAV | + | − | − | + | | | | |
| MV | | | | | + | − | − | + |

*Delutions of anti-HAV or anti-MV sera.

EXAMPLE 5

Clinical Observation for Demonstrating Safty and Immunogenicity of the Combined Divalent HM Vaccine The prospective clinical trial is performed in accordance with Chinese Reguirements for Biological Products to evoluate safty and immunogenicity of the combined hepatitis A-measles vaccine.

275 healthy infants ranged in age from 8 to 12 months are randomly devided into three groups and following respective vaccines are given: molovalent hepatitis A (group M), monovalent meales vaccine (group M), and hepatitis A with measles vaccines (simultaneously or successively injected using two separated syringes) (group HM). The stock suspensions of HAV and HV used in this Example are prepared from HAV strain L-A-1 and MV strain Change-47 and the infectious potencies (viral titers) are more than $10^{6.5}$ and $10^{4.0}$ CCID50/ml, respectively. The vaccines are vaccinated subcutaneously in the deltoid region in 1.0 ml dose for HA vaccine and 0.2 ml dose for measles vaccine.

Adverse events are recorded by using daily card of local clinical reactions (soreness, redness and swelling at injection site) for the following 72 hrs after the vaccination and of general clinical reation (fever) for 42 days following vaccination. Redness and swelling are scored as grade 1 (mild) (diameter <30 mm), grade 2 (moderate) (>30 mm) and grade 3 (severe) (>30 mm and persisting more than 24 hrs). Fever also is graded as mild (37.5–38° C.), moderate (>38.0–39.0° C.) and severe (>39° C.).

Anti-HAV and anti-MV HI antibodies, and GPT enzyme are tested prior to vaccination and on weeks 4 and 8 post-vaccination. GPT enzyme is measured in the inventor's laboratory using an automated enzyme assay. Detection of anti-HAV antibody is performed by a ELISA (commercially available from Abbott Co., Ltd.), and detection of anti-MV HI antibody is carried out according to Rosen (Rosen, L., Varology 13:139–141, 1961) using a commercially available ELISA kit.

A $X^2$ test is used to compare incidences of local and general reactions among groups. For the comparision of immunogenicity, seroconversion and seroprotection rates, and geometric mean titers (GMTs) of anti-HAV and anti-MV are calculated for each group. Differences between GMT's are determined using Student's t-test.

The observation results showed that, 2 of 103 vaccinees who simultaneously received HAV and MV vaccines (1.94%) exhibited mild general reation, and only one vaccinee (0.97%) occurred moderate reaction.

On weeks 8 post-vaccination of simultaneous HAV with MV vaccines and single HAV vaccne, 92.27% of the vaccinees are seropositive for anti-HAV antibody in group HM and 93.66% in group H, there are no significant differences between the two groups ($X^2$=0.19, p>0.05). Further, the GMTs against both HAV and MV in group HM and the GMT against HAV in group H are 5.005±2.538 and 4.886±2.610 respectively, no significant differences between the two groups are found (t=0.86, p>0.05).

Similarly, on weeks 8 post-vaccination of simultaneous HAV with MV vaccines and single MV vaccine, 98.05% of the vaccinees are seropositive for anti-MV antibody in group HM, and 96.66% in group M, there are no significant differences between the two groups ($X^2$=0.204, p>0.05). Further, the GMTs against both HAV and MV in group IM and the GMT against MV in group M are 16.22±2.29 and 13.93±2.59 respectively, there are no significant differences between the two groups are found (t=0.86, p>0.05).

What is claimed is:

1. A combined hepatitis A-measles vaccine, comprising a combination of prophylactically effective titers of attenuated hepatitis A live virus and prophylactically effective titers of attenuated measles live virus, wherein said combination does not induce any mutual interference on immune response and immunogenicity.

2. The combined hepatitis A-measles vaccine of claim 1, wherein said prophylactically effective titers of hepatitis A is not less than $10^{6.0}$ CCID50/ml, and wherein said prophylactically effective titers of measles virus is not less than $10^{3.5}$ CCID50/ml.

3. The combined hepatitis A-measles vaccine of claim 1, wherein said combined vaccine is provided in lyophilized form.

4. The combined hepatitis A-measles vaccine according to claim 1 further comprising a stabilizer, wherein said stabilizer consists essentially of from 0 to 2% (w/v) of human serum albumin, from 0.5 to 1% (w/v) of gelatin, from 5 to 10% (w/v) of trehalose, from 0.75 to 1.5% (w/v) of sodium glutamate, from 0.05 to 0.55% (w/v) of ascorbic acid, from 0.5 to 2.8% (w/v) of urea, from 5 to 10% (w/v) of mannitol or sorbitol or a 1:1 (v/v) mixture of them, and from 0.5 to 1% (w/v) of inositol, in terms of the concentration in the stabilized live vaccine.

5. The combined hepatitis A-measles vaccine according to claim 2 further comprising a stabilizer, wherein said stabilizer consists essentially of from 0 to 2% (w/v) of human serum albumin, from 0.5 to 1% (w/v) of gelatin, from 5 to 10% (w/v) of trehalose, from 0.75 to 1.5% (w/v) of sodium glutamate, from 0.05 to 0.55% (w/v) of ascorbic acid, from 0.5 to 2.8% (w/v) of urea, from 5 to 10% (w/v) of mannitol or sorbitol or a 1:1 (v/v) mixture of them, and from 0.5 to 1% (w/v) of inositol, in terms of the concentration in the stabilized live vaccine.

6. The combined hepatitis A-measles vaccine of claim 4, wherein said combined vaccine is provided in lyophilized form.

7. A method of preparing the combined hepatitis A-measles vaccine of claim 1, comprising mixing a stock material of attenuated hepatitis A live vaccine having viral titers of not less than $10^{7.0}$ CCID$_{50}$/ml with a stock material of attenuated measles live vaccine having viral titers of not less than $10^{4.5}$ CCID50/ml to yield a stock suspension of combined vaccine wherein said titers of said hepatitis A virus is not less than $10^{6.5}$ CCID$_{50}$/ml and said titers of said measles virus is not less than $10^{4.0}$ CCID$_{50}$/ml.

8. A method of preparing the combined hepatitis A-measles vaccine of claim 1, comprising the following steps:
  (a) providing a plurality of seed viruses of attenuated hepatitis A live virus and a plurality of seed viruses of attenuated measles live virus;
  (b) inoculating said seed viruses of hepatitis A virus into a human fetal lung diploid fibroblast cell culture and following by culturing the cells to propagate the virus;
  (c) when the positive hepatitis A virus-infected cells are more than 75%, inoculating said seed viruses of measles virus into the same cell monolayers on which the hepatitis A virus have propagated, and the cells are cultured continuously; and
  (d) at the time when the positive hepatitis A virus-infected cells are more than 90% as detected in terms of immunofluorescence and the positive measles virus-infected cells are more than 90% as detected in terms of cytopathogenic effect, harvesting the cells infected with the two viruses and thereby collecting the vaccine stock materials containing the two viruses to obtain the desired combined vaccine.

9. The method of claim 7, said method further comprising mixing the stock material of combined hepatitis A-measles vaccine with a stabilizer for attenuated live vaccine at about 1:1 volume ratio; and lyophilizing the resultant formulation to obtain a lyophilized preparation of the combined hepatitis A-measles vaccine.

10. The method of claim 8, said method further comprising mixing the stock material of combined hepatitis A-measles vaccine with a stabilizer for attenuated live vaccine at about 1:1 volume ratio; and lyophilizing the resultant formulation to obtain a lyophilized preparation of the combined hepatitis A-measles vaccine.

11. The method of claim 9, wherein said stabilizer for lyophilized live vaccine consists essentially of from 0 to 2% (w/v) of human serum albumin, from 0.5 to 1% (w/v) of gelatin, from 5 to 10% (w/v) of trehalose, from 0.75 to 1.5% (w/v) of sodium glutamate, from 0.05 to 0.55% (w/v) of ascorbic acid, from 0.5 to 2.8%(w/v) of urea, from 5 to 10% (w/v) of mannitol or sorbitol or a 1:1 (v/v) mixture of them, and from 0.5 to 1% (w/v) of inositol, in terms of the concentrations in the live vaccine formulation prior to lyophilization.

12. The method of claim 10, wherein said stabilizer for lyophilized live vaccine consists essentially of from 0 to 2% (w/v) of human serum albumin, from 0.5 to 1% (w/v) of gelatin, from 5 to 10% (w/v) of trehalose, from 0.75 to 1.5% (w/v) of sodium glutamate, from 0.05 to 0.55% (w/v) of ascorbic acid, from 0.5 to 2.8%(w/v) of urea, from 5 to 10% (w/v) of mannitol or sorbitol or a 1:1 (v/v) mixture of them, and from 0.5 to 1% (w/v) of inositol, in terms of the concentrations in the live vaccine formulation prior to lyophilization.

13. A method of preparing loyophilized formulations of the combined hepatitis A-measles vaccine according to claim 1, comprising the following steps:
  (a) providing stock materials containing prophylactically effective titers of attenuated hepatitis A live virus and prophylactically affective titers of attenuated measles live virus respectively, and mixing said stock materials to obtain a mixed vaccine stock;
  (b) adding a stock solution of stablizer to the mixed vaccine stock of step (a) at about 1:1 bolume ration and mixing them together to obtain a combined vaccine formulation; and
  (c) lyophilizing the combined vaccine formulation obtained from the step (b).

14. A method of preparing lyophilized formulations of the combined hepatitis A-measles vaccine according to claim 2, comprising following steps:
  (a) providing stock materials containing prophylactically effective titers of attenuated hepatitis A live virus and prophylactically affective titers of attenuated measles live virus respectively, and mixing said stock materials to obtain a mixed vaccine stock;
  (b) adding a stock solution of stabilizer to the mixed vaccine stock of step (a) at about 1:1 volume ratio and mixing them together to obtain a combined vaccine formulation; and
  (c) lyophilizing the combined vaccine formulation obtained from the step (b).

15. A method of preparing lyophilized formulations of the combined hepatitis A-measles vaccine according to claim 3, comprising following steps:
  (a) providing stock materials containing prophylactically effective titers of attenuated hepatitis A live virus and prophylactically affective titers of attenuated measles live virus respectively, and mixing said stock materials to obtain a mixed vaccine stock;
  (b) adding a stock solution of stabilizer to the mixed vaccine stock of step (a) at about 1:1 volume ratio and mixing them together to obtain a combined vaccine formulation; and
  (c) lyophilizing the combined vaccine formulation obtained from the step (b).

16. A method of preparing lyophilized formulations of the combined hepatitis A-measles vaccine according to claim 4, comprising following steps:

(a) providing stock materials containing prophylactically effective titers of attenuated hepatitis A live virus and prophylactically affective titers of attenuated measles live virus respectively, and mixing said stock materials to obtain a mixed vaccine stock;

(b) adding a stock solution of stabilizer to the mixed vaccine stock of step (a) at about 1:1 volume ratio and mixing them together to obtain a combined vaccine formulation; and (c) lyophilizing the combined vaccine formulation obtained from the step (b).

* * * * *

UNITED STATES PATENT AND TRADEMARK OFFICE
CERTIFICATE OF CORRECTION

PATENT NO. : 6,562,350 B1
DATED : May 13, 2003
INVENTOR(S) : Pengfu Wang et al.

It is certified that error appears in the above-identified patent and that said Letters Patent is hereby corrected as shown below:

Column 1,
Line 17, "intants" should be -- infants --.
Line 40, "technigues" should be -- techniques --.
Line 42, "nember" should be -- number --.
Line 50, "mupms and rubella" should be -- mumps and rubella --.

Column 2,
Line 24, "from 0.05 to 0.5%" should be -- from 0.05 to 0.55% --.
Line 48, "abserved, in particulr" should be -- observed in particular --.

Column 3,
Line 6, "the desired combined vaccife" should be -- the desired combined vaccine --.
Line 67, "desease" should be -- disease --.

Column 4,
Line 6, "two does of" should be -- two doses of --.
Line 11, "entering collage" should be -- entering college --.
Line 19, "discase caused by intection" should be -- disease caused by infection --.
Line 20, "deseases" should be -- diseases --.
Line 56, "80 milions" should be -- 80 million --.
Line 62, "production practies" should be -- production practices --.
Line 64, "exellent host" should be -- excellent host --.

Column 5,
Line 14, "suitabe volume" should be -- suitable volume --.
Line 18, "$10^6$ $CCID_{50}$" should be -- $10^{6.0}$ $CCID_{50}$ --.
Line 34, "cultured continuasly" should be -- cultured continuously --.
Line 39, "cytopatliogenic effect" should be -- cytopathogenic effect --.
Line 49, "Reguirement for" should be -- Requirement for --.
Line 50, "Reguirements for Biological" should be -- Requirements for Biological --.
Line 54, "By contract," should be -- By contact --.
Line 56, "shoter replication" should be -- shorter replication --.
Line 58, "can be bserved" should be -- can be observed --.
Line 60, "exellent susceptible" should be -- excellent susceptible --.

Column 6,
Line 6, "intected cells" should be -- infected cells --.
Line 9, "HAV-intected cells" should be -- HAV-infected cells --.
Line 14, "continuasly with" should be -- continuously with --.
Line 60, "agaist heat" should be -- against heat --.

UNITED STATES PATENT AND TRADEMARK OFFICE
CERTIFICATE OF CORRECTION

PATENT NO. : 6,562,350 B1
DATED : May 13, 2003
INVENTOR(S) : Pengfu Wang et al.

It is certified that error appears in the above-identified patent and that said Letters Patent is hereby corrected as shown below:

Column 7,
Line 15, "may shose" should be -- may choose --.
Line 45, "of geltion" should be -- of gelatin --.
Line 49, "1:1 tixture" should be -- 1:1 texture --.
Line 52, "comparason experiment" should be -- comparison experiment --.
Line 54, "HSA compnent" should be -- HSA component --.
Line 55, "for exmaple" should be -- for example --.
Line 57, "suitable adjusted" should be -- suitably adjusted --.
Line 58, "show experimentally" should be -- shown experimentally --.
Line 64, "adentifiable infectious" should be -- identifiable infectious --.

Column 8,
Line 1, "its safty and" should be -- its safety and --.
Line 2, "animals receved" should be -- animals received --.
Line 6, "Egually important" should be -- Equally important --.
Line 28, "healthy intants" should be -- healthy infants --.
Line 43, "modifired ELISA" should be -- modified ELISA --.
Line 44, "In summry," should be -- In summary, --.
Line 46, "intants and young" should be -- infants and young --.
Line 48, "for evoluation" should be -- for evaluation --.
Line 52, "viruses intection" should be -- viruses infection --.
Line 63, "two deseases" should be -- two diseases --.

Column 9,
Line 27, "continuas culturing" should be -- continuous culturing --.
Line 39, "continuasly cultured" should be -- continuously cultured --.
Line 47, "cultured continuasly" should be -- cultured continuously --.

Column 10,
Line 9, "gelation-HSA" should be -- gelatin-HSA --.
Line 16, "at about I1:1" should be -- at about 1:1 --.
Line 18, "stbilize the viruses" should be -- stabilize the viruses --.
Line 38, "conbined divalent" should be -- combined divalent --.

Column 11,
Line 34, "It is can be seen" should be -- It can be seen --.
Line 46, "exellent storage" should be -- excellent storage --.
Line 49, "safty and immunogenicity" should be -- safety and immunogenicity --.

UNITED STATES PATENT AND TRADEMARK OFFICE
CERTIFICATE OF CORRECTION

PATENT NO. : 6,562,350 B1
DATED : May 13, 2003
INVENTOR(S) : Pengfu Wang et al.

It is certified that error appears in the above-identified patent and that said Letters Patent is hereby corrected as shown below:

Column 12,
Line 1, "evoluate safty" should be -- evaluate safety --.
Line 14, "evoluated for" should be -- evaluated for --.
Line 32, "valume of HAV" should be -- volume of HAV --.
Line 37, "to allow adsorption" should be -- to allow absorption --.
Line 38, "The the plates" should be -- The plates --.

Column 13,
Line 22, "amimals pre- and" should be -- animals pre- and --.
Line 37, "Safty and Immunogenicity" should be -- Safety and Immunogenicity --.
Line 42, "Reguirements for Biological Products to evoluate safty" should be
-- Requirement for Biological Products to evaluate safety --.
Line 46, "devided into three" should be -- divided into three --.
Line 47, "molovalent hepatitis" should be -- monovalent hepatitis --.
Line 48, "meales vaccine" should be -- measles vaccine --.
Line 54, "$10^{4.0}$ CCID50/ml" should be -- $10^{4.0}$ CCID$_{50}$/ml --.

Column 14,
Line 36, "HAV vaccne" should be -- HAV vaccine --.
Line 49, "in group IM" should be -- in group HM --.
Line 62, "$10^{6.0}$ CCID50/ml" should be -- $10^{6.0}$ CCID$_{50}$/ml --.
Line 64, "$10^{3.5}$ CCID50/ml" should be -- $10^{3.5}$ CCID$_{50}$/ml --.

Column 15,
Line 29, "$10^{4.5}$ CCID50/ml" should be -- $10^{4.5}$ CCID)$_{50}$/ml --.

Column 16,
Line 31, "1:1 bolume ration" should be -- 1:1 volume ratio --.

Signed and Sealed this

Sixteenth Day of December, 2003

JAMES E. ROGAN
*Director of the United States Patent and Trademark Office*